US011219706B2

(12) United States Patent
Giare-Patel et al.

(10) Patent No.: US 11,219,706 B2
(45) Date of Patent: Jan. 11, 2022

(54) ENHANCED FORMULATIONS FOR COATING MEDICAL DEVICES

(71) Applicant: Arrow International, Inc., Wayne, PA (US)

(72) Inventors: Kamma Giare-Patel, Reading, PA (US); Nisha Gupta, Reading, PA (US); Greg Etter, Reading, PA (US); Kevin Sechrist, Reading, PA (US); Molly Stewart, Reading, PA (US); Igor Tentler, Reading, PA (US); Al Williams, Reading, PA (US)

(73) Assignee: ARROW INTERNATIONAL LLC, Morrisville, NC (US)

( * ) Notice: Subject to any disclaimer, the term of this patent is extended or adjusted under 35 U.S.C. 154(b) by 0 days.

(21) Appl. No.: 16/786,791

(22) Filed: Feb. 10, 2020

(65) Prior Publication Data

US 2020/0171211 A1 Jun. 4, 2020

Related U.S. Application Data

(60) Continuation of application No. 14/357,440, filed as application No. PCT/US2012/064203 on Nov. 8, 2012, now abandoned, which is a continuation-in-part of application No. 13/292,636, filed on Nov. 9, 2011, now abandoned, which is a division of application No. 12/401,829, filed on Mar. 11, 2009, now abandoned.

(60) Provisional application No. 61/605,590, filed on Mar. 1, 2012.

(51) Int. Cl.
| | |
|---|---|
| *A61L 29/16* | (2006.01) |
| *A61L 29/06* | (2006.01) |
| *A61L 29/08* | (2006.01) |
| *A61L 29/10* | (2006.01) |
| *A61M 25/00* | (2006.01) |

(52) U.S. Cl.
CPC ............... *A61L 29/16* (2013.01); *A61L 29/06* (2013.01); *A61L 29/08* (2013.01); *A61L 29/085* (2013.01); *A61L 29/106* (2013.01); *A61M 25/0009* (2013.01); *A61M 25/0045* (2013.01); *A61F 2250/0067* (2013.01); *A61L 2202/24* (2013.01); *A61L 2300/104* (2013.01); *A61L 2300/114* (2013.01); *A61L 2300/206* (2013.01); *A61L 2300/404* (2013.01); *A61L 2300/406* (2013.01); *A61L 2300/42* (2013.01); *A61L 2300/442* (2013.01); *A61L 2300/45* (2013.01); *A61L 2420/02* (2013.01); *A61L 2420/06* (2013.01); *A61M 2025/0056* (2013.01)

(58) Field of Classification Search
CPC ........ A61L 29/09; A61L 29/06; A61L 29/106; A61L 29/085; A61M 25/0009; A61M 25/0045

See application file for complete search history.

(56) References Cited

U.S. PATENT DOCUMENTS

| | | | |
|---|---|---|---|
| 4,925,668 A | 5/1990 | Khan et al. | |
| 5,091,205 A | 2/1992 | Fan | |
| 5,165,952 A | 11/1992 | Solomon et al. | |
| 5,489,269 A | 2/1996 | Aldrich et al. | |
| 5,536,241 A | 7/1996 | Zapol | |
| 5,616,338 A | 4/1997 | Fox, Jr. et al. | |
| 5,707,366 A | 1/1998 | Solomon et al. | |
| 5,707,385 A | 1/1998 | Williams | |
| 5,797,887 A | 8/1998 | Rosen et al. | |
| 5,942,239 A | 8/1999 | Huprich et al. | |
| 6,039,755 A | 3/2000 | Edwin et al. | |
| 6,517,548 B2 | 2/2003 | Lorentzen Cornelius et al. | |
| 6,530,951 B1 | 3/2003 | Bates et al. | |
| 6,556,217 B1 | 4/2003 | Makipaa et al. | |
| 6,565,591 B2 | 5/2003 | Brady et al. | |
| 6,656,217 B1 | 12/2003 | Herzog, Jr. et al. | |
| 6,872,195 B2 * | 3/2005 | Modak .................... | A61L 27/34 424/422 |
| 7,008,979 B2 | 3/2006 | Schottman et al. | |
| 7,029,467 B2 | 4/2006 | Currier et al. | |
| 7,655,021 B2 | 2/2010 | Brasington et al. | |
| 7,803,395 B2 | 9/2010 | Datta et al. | |
| 7,892,469 B2 | 2/2011 | Lim et al. | |
| 8,017,686 B2 | 9/2011 | Buter et al. | |
| 2003/0203991 A1 | 10/2003 | Schottman et al. | |
| 2004/0052831 A1 | 3/2004 | Modak et al. | |
| 2004/0117007 A1 | 6/2004 | Whitbourne et al. | |
| 2004/0208908 A1 | 10/2004 | Modak et al. | |

(Continued)

FOREIGN PATENT DOCUMENTS

| | | |
|---|---|---|
| EP | 0379269 A2 | 7/1990 |
| EP | 1704879 A1 | 9/2006 |

(Continued)

OTHER PUBLICATIONS

Clarwyn Yip, et al., "Hickman catheter-related infections in patients with cancer", International Journal of Antimicrobial Agents, 1998, pp. 181-189, vol. 10, issue No. 3 [Cited in related U.S. Appl. No. 12/401,829].

(Continued)

*Primary Examiner* — Blessing M Fubara
(74) *Attorney, Agent, or Firm* — BakerHostetler

(57) ABSTRACT

Provided are formulations and related methods, for coating or impregnating a medical device, as well as a coated or impregnated medical device, for example, a device that is a catheter or cannula, where a different formulation may be used for interior surface of device and for exterior surface of the device.

5 Claims, 9 Drawing Sheets

(56) References Cited

U.S. PATENT DOCUMENTS

Figure 1:
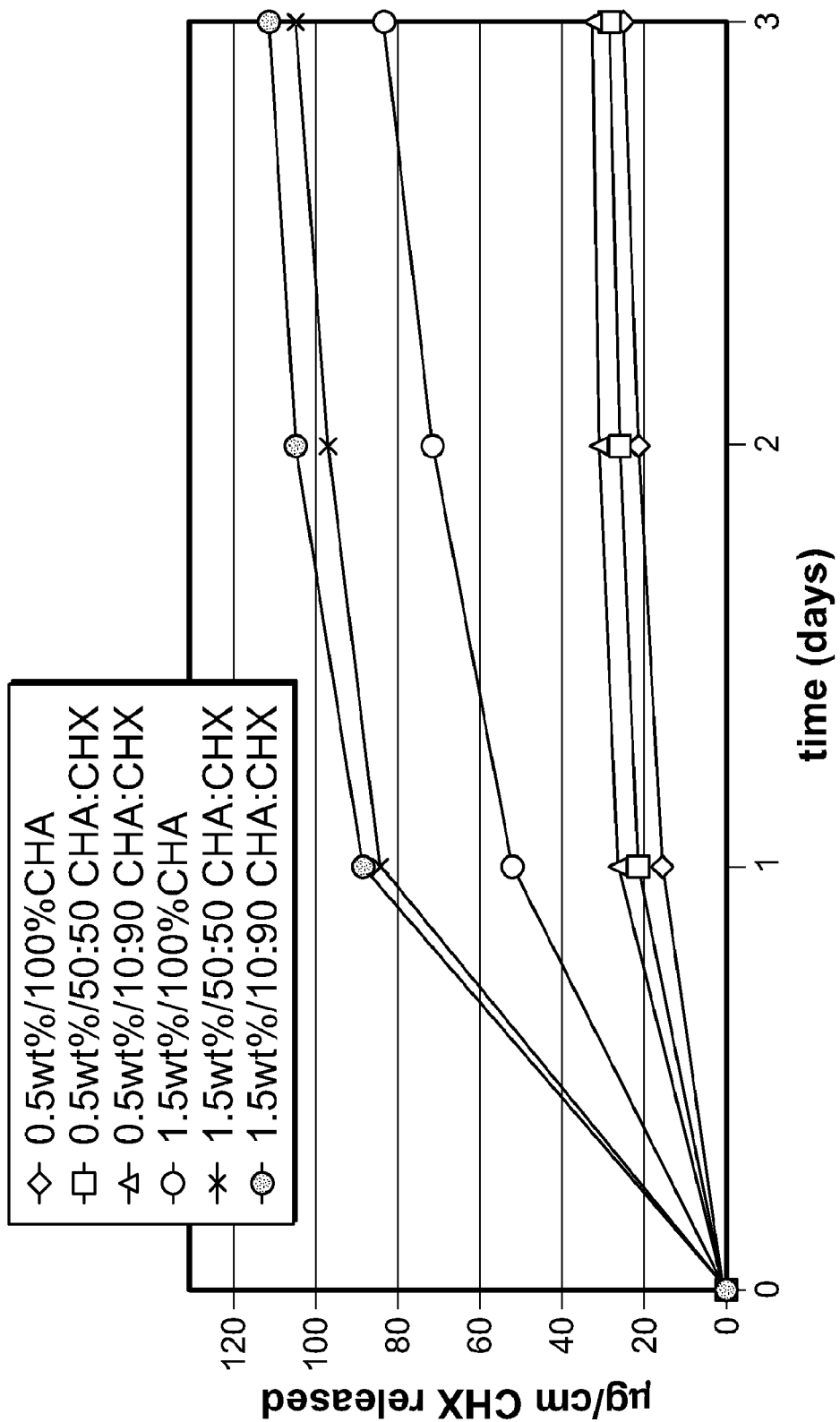

| | | |
|---|---|---|
| 2004/0247640 A1 | 12/2004 | Zhao et al. |
| 2005/0131356 A1 | 6/2005 | Ash et al. |
| 2005/0197634 A1 | 9/2005 | Raad et al. |
| 2006/0194008 A1 | 8/2006 | Schwartz et al. |
| 2007/0010702 A1 | 1/2007 | Wang et al. |
| 2007/0048345 A1 | 3/2007 | Huang et al. |
| 2007/0127488 A1 | 6/2007 | Futenma et al. |
| 2007/0129690 A1 | 6/2007 | Rosenblatt et al. |
| 2007/0202177 A1 | 8/2007 | Hoang |
| 2007/0207335 A1 | 9/2007 | Karandikar et al. |
| 2007/0224235 A1 | 9/2007 | Tenney et al. |
| 2007/0248676 A1 | 10/2007 | Stamler et al. |
| 2008/0014557 A1 | 1/2008 | Kuhn et al. |
| 2009/0214674 A1 | 8/2009 | Barraud et al. |
| 2010/0069854 A1 | 3/2010 | Okoh et al. |
| 2010/0082097 A1 | 4/2010 | Rosenblatt et al. |
| 2010/0234815 A1 | 9/2010 | Do et al. |
| 2011/0054581 A1 | 3/2011 | Desai et al. |
| 2011/0305895 A1 | 12/2011 | Roth et al. |
| 2013/0108707 A1* | 5/2013 | Shalaby ............... A61K 47/34 424/618 |

FOREIGN PATENT DOCUMENTS

| | | |
|---|---|---|
| KR | 20110100247 A | 9/2011 |
| WO | 0170199 A1 | 9/2001 |
| WO | 0234311 A2 | 5/2002 |
| WO | 2006100156 A2 | 9/2006 |
| WO | 2006125262 A1 | 11/2006 |
| WO | 2007127488 A1 | 11/2007 |
| WO | 2008150375 A1 | 12/2008 |

OTHER PUBLICATIONS

David L. Veenstra, et al., "Efficacy of Antiseptic-Impregnated Central Venous Catheters in Preventing Catheter-Related Bloodstream Infection: A meta-analysis", JAMA, Jan. 20, 1999, pp. 261-267, vol. 281, issue No. 3 [Cited in related U.S. Appl. No. 12/401,829].

Dolores Vernet, et al., "Effect of nitric oxide on the differentiation of fibroblasts into myofibroblasts in the Peyronie's fibrotic plaque and in its rat model", Nitric Oxide, 2002, pp. 262-276 [Cited in related U.S. Appl. No. 12/401,829].

Ferric C. Fang, "Mechanisms of Nitric Oxide-related Antimicrobial Activity", Journal of Clinical Investigations, Jun. 1997, pp. 2818-2825, vol. 99, issue No. 12 [Cited in related U.S. Appl. No. 12/401,829].

Guang-Rong Wang, et al., "Mechanism of platelet inhibition by nitric oxide: In vivo phosphorylation of thromboxane receptor by cyclic GMP-dependent protein kinase", Proceedings of the National Academy of Science USA, Apr. 1998, pp. 4888-4893, vol. 95 [Cited in related U.S. Appl. No. 12/401,829].

Huiping Zhang, et al., "Nitric oxide releasing silicone rubbers with improved blood compatibility: preparation, characterization and in vivo evaluation", Biomaterials, 2002, pp. 1485-1494, vol. 23 [Cited in related U.S. Appl. No. 12/401,829].

Issam Raad, et al., "Central Venous Catheters Coated with Minocycline and Rifampin for the Prevention of Catheter-Related Colonization and Bloodstream Infections: A Randomized, Double-Blind Trial", Annals of Internal Medicine, • Aug. 15, 1997, pp. 267-274, vol. 127, issue No. 4 [Cited in related U.S. Appl. No. 12/401,829].

Jae Ho Shin, et al., "Improving the biocompatability of in vivo sensors via nitric oxide release", Analyst, 2006, pp. 609-615, vol. 131 [Cited in related U.S. Appl. No. 12/401,829].

Mark H. Schoenfisch, et al., "Improving the Thromboresistivity of Chemical Sensors via Nitric Oxide Release: Fabrication and in Vivo Evaluation of NO-Releasing Oxygen-Sensing Catheters", Analytical Chemistry, Mar. 15, 2000, pp. 1119-1126, vol. 72, issue No. 6 [Cited in related U.S. Appl. No. 12/401,829].

Megan C. Frost, et al., "In Vivo Biocompatibility and Analytical Performance of Intravascular Amperometric Oxygen 11 Sensors Prepared with Improved Nitric Oxide-Releasing Silicone Rubber Coating", Analytical Chemistry, Dec. 1, 2002, pp. 5942-5947, vol. 74, issue No. 23 [Cited in related U.S. Appl. No. 12/401,829].

Paul Jurasz, et al., "Nitric Oxide and Platelet Function", Nitric Oxide: Biology and Pathobiology, 2000, pp. 823-840, edited by Louis J_ Ignarro, Academic Press, San Diego [Cited in related U.S. Appl. No. 12/401,829].

Robert M. Clancy, et al., "The Role of Nitric Oxide in Inflammation and Immunity", Arthritis & Rheumatism, Jul. 1998, pp. 1141-1151, vol. 41, issue No. 7 [Cited in related U.S. Appl. No. 12/401,829].

Stefan Carlsson, et al., "Intravesical Nitric Oxide Delivery for Prevention of Catheter-Associated Urinary Tract Infections", Antimicrobial Agents and Chemotherapy, Jun. 2005, pp. 2352-2355, vol. 49, issue No. 6 [Cited in related U.S. Appl. No. 12/401,829].

Victor D. Rosenthal, et al., "Device-Associated Nosocomial Infections in 55 Intensive Care Units of 8 Developing Countries", Annals of Internal Medicine, Oct. 17, 2006, pp. 582-591, vol. 145, issue No. 8 [Cited in related U.S. Appl. No. 12/401,829].

Yiduo Wu, et al., "Improving blood compatibility of intravascular oxygen sensors via catalytic decomposition of S-nitrosothiols to generate nitric oxide in situ", Sensors and Actuators B, 2007, pp. 36-46, vol. 121 [Cited in related U.S. Appl. No. 12/401,829].

Rifampicin, Wikipedia [Downlaoded May 23, 2011] [Retrieved from internet URL: http://en.wikipedia.ofg.wiki/Rifampicin ], 1 page [Cited in related U.S. Appl. No. 12/401,829].

WIPO Patentscope, Bibliographic data for Barraud et al., WO/2006/125262, PCT/AU2006/000693—included to document that the international application was published in English (see p. 2) [Downloaded Nov. 16, 2012], 2 pages [Cited in related U.S. Appl. No. 13/292,636].

* cited by examiner

ENHANCED FORMULATIONS FOR COATING MEDICAL DEVICES

CROSS-REFERENCE TO RELATED APPLICATIONS

This present application is a continuation of U.S. application Ser. No. 14/357,440, filed May 9, 2014, which claims priority of International Application No.: PCT/US2012/064203, filed Nov. 8, 2012, which claims priority of U.S. Provisional Application 61/605,590, filed Mar. 1, 2012, and claims priority of continuation application Ser. No. 13/292,636, filed Nov. 9, 2011, which is a division of U.S. application Ser. No. 12/401,829, filed Mar. 11, 2009, the entire contents of which are hereby incorporated by reference in their entirety.

FIELD OF THE DISCLOSURE

The present disclosure relates in particular to formulations for coating medical devices, the combination of medical device in contact with coating solution, methods for coating or impregnated medical device, a coated or impregnated medical device, and methods for clinical use of coated medical device.

BACKGROUND OF THE DISCLOSURE

Catheters and other devices that are implanted into vessels or cavities in the clinical or veterinary situation are associated with infections, including biofilms on the medical device, local infections, and bloodstream infections. Catheter-related bloodstream infections affect over 2 million hospitalized patients per year (Krein, et al (2007) Mayo Clin. Proc. 82:672-678). Certain catheters are accessed multiple times per day, for example, for taking measurements or obtaining samples for laboratory analysis. Multiple samplings increase the potential for contamination and infections. Short-term catheters are more associated with microbial contamination of the external surface of the catheter, while internal surface or lumenal microbial colonization is associated with long-term implantation. Catheters, catheter cuffs, and other medical devices are sometimes coated or impregnated with antimicrobial or antiseptic agents, with the goal of decreasing infections. Use of catheters impregnated with agents, such as chlorhexidine, can partially reduce the risk of infections (see, e.g., Trautner and Darouiche (2004) Arch. Intern. Med. 164:842-850). Chlorhexidine has been used for coating medical devices, including catheters, cuffs, and synthetic membranes (see, e.g., O'Grady, et al (2002) Pediatrics 110:e51-e75; Chen, et al (2003) J. Periodontol. 74:1652-1659). This agent has broad activity against gram positive and negative bacteria, as well as against yeasts and some viruses (Milstone, et al. (2008) Healthcare Epidemiology 46:274-281).

SUMMARY OF THE DISCLOSURE

Briefly stated, the disclosure provides a first formulation for coating or impregnating a medical device, the formulation comprising: methyl-ethyl-ketone (50-70%); methanol (10-20%); acetone (15-25%); chlorhexidine diacetate (0.5-4%); and chlorhexidine free base (0.5-4%). Also provided is the above formulation, wherein the medical device has an interior surface defining a cavity or lumen, and an exterior surface, wherein the formulation is configured for coating or impregnating the interior surface of the medical device with an anti-microbiologically effective amount of chlorhexidine. In exclusionary embodiments, what is provided is above formulation, that does not contain triclosan, that does not contain a silver salt, that does not contain a combination of triclosan and silver salt, or that does not contain zinc.

In a second formulation, what is provided is a formulation for coating or impregnating a medical device, the formulation comprising: tetrahydrofuran (THF) (70-90% by weight); methanol (5-15%); polyurethane (1-15%); and chlorhexidine diacetate (0.5-4.0%). The second formulation also encompasses the above formulation, wherein the polyurethane is 95A polyurethane. Also provided is the above formulation, wherein the medical device has an interior surface defining a cavity or lumen, and an exterior surface, wherein the formulation is configured for coating or impregnating the exterior surface of the medical device with an anti-microbiologically effective amount of chlorhexidine. In exclusionary embodiments, second formulation does not comprise triclosan, that does not comprise a silver salt, that does not comprise the combination of triclosan and silver salt, or that does not comprise zinc. Alternative formulations include, instead of polyurethane, a polymer that is not polyurethane, such as polystyrene, polypropylene, polyacrylate, polymethacrylate, polyacrylamide, polysilane, polysiloxane, and any combination thereof.

In medical device embodiments, what is provided is a medical device comprising an interior surface that defines a cavity or lumen, and an exterior surface, wherein the interior surface is treated with the first formulation, resulting in coating or impregnation with an antimicrobially effective amount of chlorhexidine, wherein the exterior surface of the medical device is treated with the second formulation, resulting in coating or impregnation with an antimicrobially effect amount of chlorhexidine. Also provided is above medical device, wherein the treated medical device has a burst pressure that is selected from at least 250, at least 260, at least 270, at least 280, at least 290, and at least 300 pounds per square inch (psi). Also provided is above medical device, that comprises one or more of a catheter, cannula, introducer, dilator, or sheath. In exclusionary embodiments, what is provided is above medical device that does not comprise triclosan, does not comprise silver salt, does not comprise the combination of triclosan and silver salt, or does not comprise zinc.

In methods embodiments, what is provided is a method for coating or impregnating a medical device, the medical device comprising an inside surface, and a cavity or lumen that is defined by said inside surface, wherein the medical device further comprises an outside surface or exterior surface, wherein the method comprises contacting a first formulation to the inside surface, and contacting a second formulation to the outside surface, and where the first and second formulations have a different composition from each other. Also provided is above method, wherein the second formulation comprises a dissolved polymer. Also provided is above method, wherein the second formulation includes a dissolved polymer that comprises polyurethane. Alternative formulations include, instead of polyurethane, a polymer that is not polyurethane, such as polystyrene, polypropylene, polyacrylate, polymethacrylate, polyacrylamide, polysilane, polysiloxane, and any combination thereof.

In other methods embodiments, what is encompassed is above method, wherein the first formulation is the first formulation, and the second formulation is the above-disclosed second formulation. Also provided is above method, wherein the first formulation comprises methyl-ethyl-ketone, methanol, and acetone, and under 10% tetrahydrofuran, and the second formulation comprises tetrahydrofuran, methanol, and a dissolved plastic polymer, and under 10% methyl-ethyl-ketone. Also provided is above method, comprising contacting of the first formulation to the inside surface resulting in the coating or impregnation to the inside surface of an anti-microbially effective amount of chlorhexidine, and comprising contacting of the second formulation to the outside surface resulting in the coating or impregnation to the outside surface of an anti-microbially effective amount of chlorhexidine.

In medical device embodiments, what is provided is a medical device prepared by any one of the above methods. Encompassed is medical device that comprises one or more of a catheter, cannula, introducer, dilator, or sheath. In exclusionary embodiments, what is encompassed is above medical device, wherein the medical device does not comprise triclosan, does not comprise a silver salt, does not comprise the combination of triclosan and silver salt, or does not comprise zinc.

Combination embodiments are provided. The disclosure provides combination of a medical device with the formulation of one or both of first formulation or second formulation, wherein the medical device contacts the formulation of first formulation, contacts the formulation of second formulation, or simultaneously contacts both the first formulation and the second formulation.

Methods of manufacturing are also embraced. What is embraced is a method for manufacturing the first formulation, comprising combining and mixing at least two of said methyl-ethyl-ketone, methanol, acetone, chlorhexidine diacetate, and chlorhexidine free base, wherein said combining and mixing completes the combining together of all of said methyl-ethyl-ketone, methanol, acetone, chlorhexidine diacetate, and chlorhexidine free base. What is embraced is a method for manufacturing the second formulation, comprising combining and mixing at least two of said tetrahydrofuran (THF), methanol, polyurethane, and chlorhexidine diacetate, wherein said combining and mixing completes the combining together of all of said tetrahydrofuran (THF), methanol, polyurethane, and chlorhexidine diacetate. What is provided is first formulation that includes at least one anti-thrombogenic agent. What is provided is second formulation that includes at least one anti-thrombogenic agent. Exclusionary embodiments that are provided is first formulation that does not include an anti-thrombogenic agent, as well as second formulation that does not include an anti-thrombogenic agent.

Embodiments that result in reduced thickening of intima are provided, including any one of the above medical devices that results in reduced intima thickening following dwelling in a vein, when compared to a control medical device. What is provided is above medical device, wherein the control device is treated with a formulation that does not contain chlorhexidine, or wherein the control device is not treated with any formulation. What is provided is any one of above medical devices, that does not further comprise an anti-thrombogenic agent, wherein in use and with continued residence in a subject for at least one week, thrombogenesis occurs at a reduced rate of thrombus formation, wherein the reduced rate is tested by comparing the rate (X thrombi/week) of thrombus formation associated with said medical device, with the rate (Y thrombi/week) of thrombus formation associated with a corresponding medical device that does is not coated or impregnated with chlorhexidine. What is provided is above medical device, wherein X is selected from one of less than 90% of Y, less than 80% of Y, and less than 70% of Y. What is provided is any one of above medical devices, that further comprises at least one anti-thrombogenic agent, wherein the at least one anti-thrombogenic agent is provided separately from the first formulation and second formulation. What is provided is any one of above medical devices, that configured to introduce fluids into a subject, to withdraw fluids from the subject, or to both introduce and withdraw fluids, wherein in operation the device is capable of dwelling in a physiological vessel or chamber, and is capable of introducing, withdrawing, or both introducing and withdrawing fluids to said physiological vessel or chamber, wherein in use the fluids are in contact with and transmitted by said cavity or lumen that is defined by said inside surface during the introducing and withdrawing. What is provided is above medical device, wherein the vessel is a vein.

What is provided is the above method, wherein the first formulation comprises methyl-ethyl-ketone, methanol, and acetone, and under 10% tetrahydrofuran, and the second formulation comprises tetrahydrofuran, methanol, and a dissolved plastic polymer, and under 10% methyl-ethyl-ketone.

Moreover, the disclosure provides the above method, wherein the medical device comprises a catheter or cannula. In device embodiment, what is provided is a medical device prepared by one or more of the above methods of, wherein the medical device comprises chlorhexidine, or comprises detectable chlorhexidine. In yet another methods embodiment, disclosure provides a method for using the above medical device, wherein in use, the medical device is inserted into a vascular lumen of a subject or patient, the medical device dwells in the vascular lumen for a period of at least ten seconds, and wherein the medical is removed from the vascular lumen. In exclusionary or negative embodiments, the disclosure provides any one of the above-disclosed medical devices, where the medical device does not comprise triclosan, does not comprise silver salt, or does not comprise triclosan and does not comprise silver salt. In another aspect, the disclosure excludes formulation that comprises zinc acetate, excludes a formulation comprising zinc lactate, excludes a formulation comprising a water-soluble zinc salt, or excludes any combination of the above. In embodiments, the disclosure excludes a formulation that comprises panthenol, octoxyglycerin, phenoxyethanol, iodine compound, or parachlorometaxylenol, and that excludes any combination of the above. In other exclusionary embodiments, what is excluded is a formulation that comprises octoxyglycerin, miconazole, or the combination of octoxyglycerin and miconazole.

Device exclusionary embodiments encompass the following. Without implying any limitation to the present disclosure, device exclusionary embodiments can exclude a device coated with, or impregnated with zinc acetate, zinc lactate, a water-soluble zinc salt, panthenol, octoxyglycerin, phenoxyethanol, iodine compound, parachlorometaxylenol, octoxyglycerin, miconazole, combination of oxtoxyglycerin and miconazole, or any exclusionary combination of the above.

In time embodiments, method of treatment of medical device with formulation comprises contacting medical device with formulation for 30 seconds or less, 60 seconds or less, 2 min or less, 4 min or less, 6 min or less, 8 min or less, 10 min or less, 15 min or less, 20 min or less, 30 min or less, 40 min or less, 50 min or less, 60 min or less, 2 h or less, 3 h or less, 4 h or less, and the like. Other time embodiments include 30-60 sec, 1 min-2 min, 2 min-4 min, 1 min-4 min, 1 min-5 min, 5 min-10 min, 5 min-20 min, 10 min-60 min, and the like. What is contemplated is contacting, treating, dipping, coating, impregnating, a time that ensures that an anti-microbially effective amount of anti-microbial agent is coated or impregnated, any combination thereof, and the like. In other time embodiments, external coating time is less than 10 seconds, less than 8 sec, less than 6 sec, less than 4 sec, less than 3 sec, less than 2 sec, less than 1 sec, less than 0.8 sec, less than 0.6 sec, less than 0.4 sec, and so on, where a thin, uniform layer of solution is applied to the exterior, and immediately starts to dry. In embodiments, there is no true "immersion" during external coating. Timing of internal coating can be controlled by pressurized blow-out, to remove solvent from interior of medical device. Internal coating time is about 4 seconds, about 6 sec, about 8 sec, about 10 sec, about 12 sec, about 14 sec, about 16 sec, about 18 sec, about 20 sec, about 25 sec, about 30 sec, about 40 sec, about 60 sec, about 90 sec, about 2 min, about 4 min, about 6 min, about 8 min, about 10 min, and so on.

In soluble polymer embodiments, what is provided is a formulation containing about 0.2%, about 0.5%, about 1.0%, about 1.5%, about 2.0%, about 2.5%, about 3.0%, about 3.5%, about 4.0%, about 4.5%, about 5.0%, about 6.0%, about 7.0%, about 8.0%, about 9.0%, about 10%, and the like, of soluble polymer, such as soluble polyurethane. In other aspects, what is provided is a formulation with greater than 0.2%, 0.5%, 1.0%, 1.5%, 2.0%, 2.5%, 3.0%, 3.5%, 4.0%, 4.5%, 5.0%, 6.0%, 7.0%, 8.0%, 9.0%, greater than 10%, and the like, or lesser than 0.2%, 0.5%, 1.0%, 1.5%, 2.0%, 2.5%, 3.0%, 3.5%, 4.0%, 4.5%, 5.0%, 6.0%, 7.0%, 8.0%, 9.0%, lesser than 10%, and the like, of soluble polymer.

In methods embodiment, the present disclosure provides method for coating or impregnating a medical device, the medical device comprising an inside surface, and a cavity or lumen that is defined by said inside surface, wherein the medical device further comprises an outside surface or exterior surface, wherein the method comprises contacting a first formulation to the inside surface, and contacting a second formulation to the outside surface, and where the first and second formulations have a different composition from each other. In yet another methods embodiment, the disclosure provides the above method wherein the second formulation comprises a dissolved polymer, as well as the above method wherein the dissolved polymer of the second formulation comprises polyurethane, as well as the above method, wherein the first formulation is the above formulation (that does not include polyurethane), and the second formulation (the formulation including polyurethane). In yet another methods embodiment, the present disclosure provides the above method, wherein the first formulation comprises methyl-ethyl-ketone, methanol, and acetone, and under 10% tetrahydrofuran, and the second formulation comprises tetrahydrofuran, methanol, and a dissolved plastic polymer, and under 10% methyl-ethyl-ketone. In yet another methods embodiment, what is provided is the above method, comprising contacting of the above formulation (that does not include polyurethane) to the inside surface resulting in the coating or impregnation to the inside surface of an anti-microbially effective amount of chlorhexidine, and comprising contacting of the above formulation (that does include polyurethane) to the outside surface resulting in the coating or impregnation to the outside surface of an anti-microbially effective amount of chlorhexidine. In a device embodiment, the present disclosure provides a medical device provided by the above method, as well as a medical device that comprises a catheter, cannula, or introducer. In exclusionary embodiments, the above medical device does not comprise triclosan, does not comprise a silver salt, or does not comprise the combination of triclosan and silver salt.

What is also provided is the combination of medical device and a formulation, for example, combinations where medical device is being soaked in formulation, where medical device is being partially or fully submersed in formulation, or where medical device is being perfused with formulation. Present invention provides combination of a medical device with the formulation of one or both of the above formulations (the one not including polyurethane; the one including polyurethane).

In manufacturing embodiments, present disclosure includes a method for manufacturing the above formulation (the formulation not including polyurethane), comprising combining and mixing at least two of said methyl-ethyl-ketone, methanol, acetone, chlorhexidine diacetate, and chlorhexidine free base, wherein said combining and mixing completes the combining together of all of said methyl-ethyl-ketone, methanol, acetone, chlorhexidine diacetate, and chlorhexidine free base. In another manufacturing embodiment, what is provided is a method for manufacturing the above formulation (the formulation that includes polyurethane), comprising combining and mixing at least two of said tetrahydrofuran (THF), methanol, polyurethane, and chlorhexidine diacetate, wherein said combining and mixing completes the combining together of all of said tetrahydrofuran (THF), methanol, polyurethane, and chlorhexidine diacetate. In another manufacturing embodiment, what is provided is a method for coating or impregnating a medical device with chlorhexidine, wherein the medical device comprises an interior surface and exterior surface, comprising contacting the interior surface with the above formulation (not including polyurethane), resulting in coating the interior surface with an anti-microbially effective amount of chlorhexidine, or contacting the exterior surface with the above formulation (the formulation that does include polyurethane), resulting in coating the exterior surface with an anti-microbially effective amount of chlorhexidine, or contacting both the interior surface with the above formulation of (not including polyurethane) and the exterior surface with the above formulation (formulation that does include polyurethane), resulting in resulting in coating the interior surface and the exterior surface with an anti-microbially effective amount of chlorhexidine.

"Coating" encompasses, and is not limited to, impacting to at least a surface of a device at least one of antimicrobials and anti-thrombogenic agents, and the objects of such. A coating can include, without limitation, an agent that is embedded within the coating, an agent that is surface-associated to the coating's exterior, an agent that is covalently linked to the coating (to interior, to exterior, or to both aspects of the coating), that is non-covalently linked to the coating (to interior, to exterior, or to both aspects of the coating), and any combination thereof. The agent can be, for example, chlorhexidine.

Anti-thrombogenic agent can be one or more of, for example, heparin, urokinase, streptokinase, Warfarin, dicoumarol, tissue plasminogen activator (TPA). Although chlorhexidine is not an "anti-thrombogenic agent," or is not classified as an "anti-thrombogenic agent," the present disclosure provides medical devices coated or impregnated with chlorhexidine, where an effect of this chlorhexidine is that of anti-thrombogenicity.

What is provided is a medical device where one or more anti-thrombogenic agents is provided by a first formulation, by a second formulation, by both a first formulation and a second formulation, or by way of a formulation that is not the first or second formulation.

The skilled artisan will understand that the antimicrobial agent of the present disclosure prevents or reduced microbial growth on a medical device, such as a catheter, dilator, sheath, valve. The skilled artisan will understand that use of an agent to reduce growth of bacteria, fungi, or other microbes on a medical device does not constitute a method of medical treatment. The skilled artisan will also understand that anti-thrombogenic agent of the present disclosure concerns an interaction between a medical device and one or more enzymes or proteins, and that this is not a method of medical treatment.

What is embraced by a formulation for external application or soaking that comprises a dissolved plastic polymer. The dissolved plastic polymer can be more or more of, or any combination of, polyurethane, polyethylene, polyethlyene teraphthalate, ethylene vinyl acetate, silicone, tetrafluoroethylene, polypropylene, polyethylene oxide, polyacrylate, and so on. What is encompassed are coatings, coating solutions, and medical devices that are coated with coating solutions, using Carbothane® family of polycarbonate-based aliphatic and aromatic polyurethanes, Estane®, which is a thermoplastic polyurethane, Pellethane®, which is a family of medical-grade polyurethane elastomers and exceptionally smooth surfaces, Tecoflex®, which is a family of aliphatic polyether polyurethanes, where low durometer versions are particularly suitable for long-term implant applications, Tecothane®, an aromatic polyurethane, Texin®, an aromatic polyether-based polyurethane which allows for very thin gauges (Microspec Corp., Peterborough, N.H.; Lubrizol, Inc., Wickliffe, Ohio; Entec Polymers, Orlando, Fla.). See, U.S. Pat. No. 6,565,591 of Brady, U.S. Pat. No. 7,029,467 of Currier, and U.S. Pat. No. 7,892,469 of Lim, which are hereby incorporated by reference in their entirety. In embodiments, the present disclosure provides the recited polymers for use in coating solutions, or for use in manufacturing the medical device that is to be coated. In exclusionary embodiments, what is provided is a formulation for coating, or a medical device coated with said coating, where the only polymer in the coating is Tecoflex, Texothane, Texin, Carbothane, Estane, or Pellethane. For example, what is provided is a formulation that does not include Pellethane.

In embodiments where an interior is treated with a first formulation (A) and an exterior is treated with a second formulation (B), contact of the interior by the first formulation (A) and contact of the same interior by the second formulation (B) occurs, in some embodiments, at a ratio of greater than (A)/(B)=80/20, greater than (A)/(B)=85/15, greater than (A)/(B)=90/10, greater than (A)/(B)=95/5, greater than (A)/(B)=98/2, greater than (A)/(B)=99/1, greater than (A)/(B)=99.9/0.1, and so on. What is also contemplated, are embodiments where an exterior is treated with a first formulation (C) and an interior is treated with a second formulation (D), contact of the exterior by the first formulation (C) and contact of the same exterior by the second formulation (D) occurs, in certain embodiments, at a ratio of greater than (C)/(D)=80/20, greater than (C)/(D)=85/15, greater than (C)/(D)=90/10, greater than (C)/(D)=95/5, greater than (C)/(D)=98/2, greater than (C)/(D)=99/1, greater than (C)/(D)=99.9/0.1, and so on.

BRIEF DESCRIPTIONS OF THE FIGURES

FIG. 1. Cumulative elution of chlorhexidine (micrograms/cm) over time, where treatment of catheters was with 0.5% or 1.5% chlorhexidine.

Figure 2:
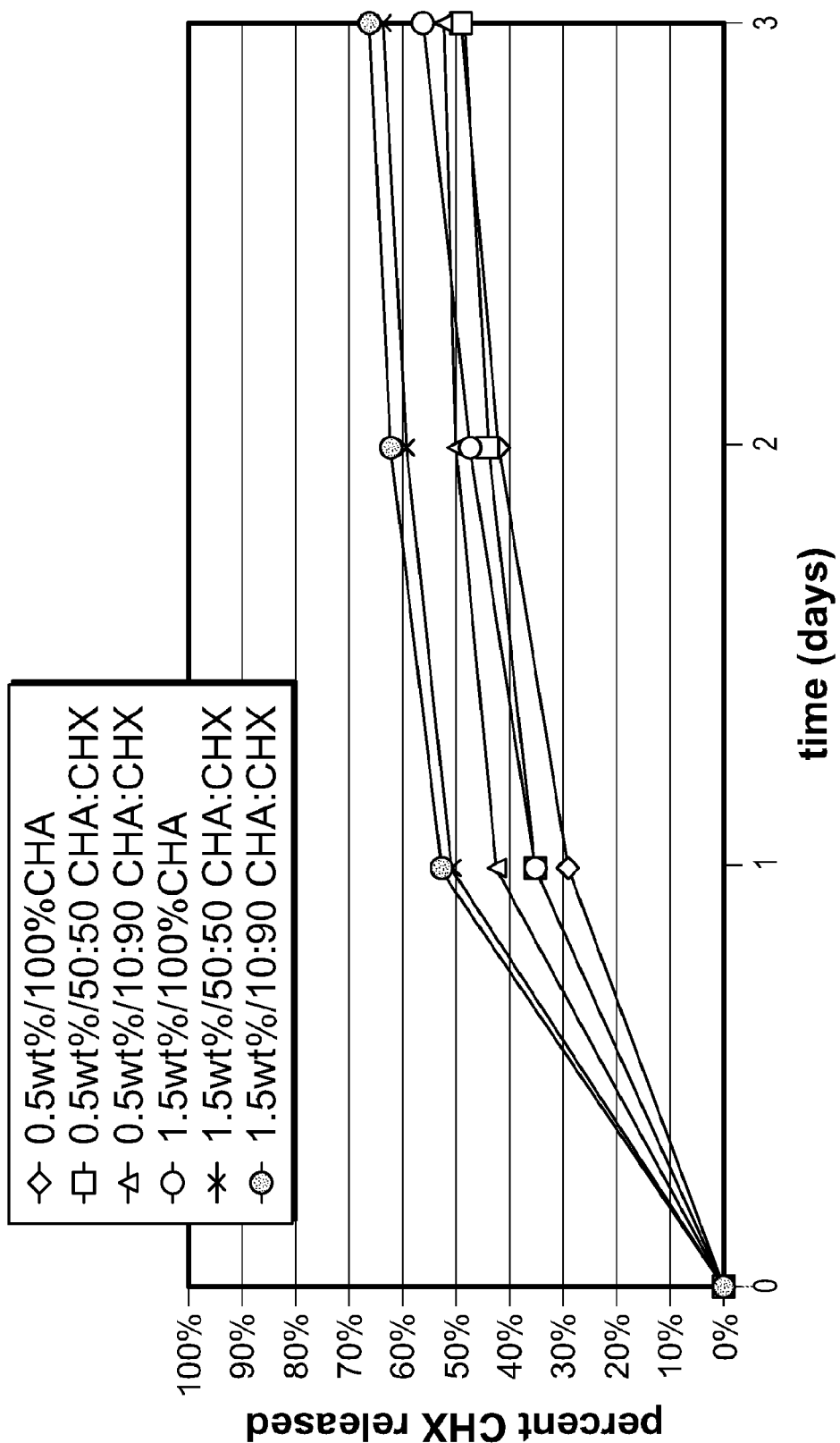

FIG. 2. Cumulative elution of chlorhexidine (percent release) over time, where treatment of catheters was with 0.5% or 1.5% chlorhexidine.

Figure 3:
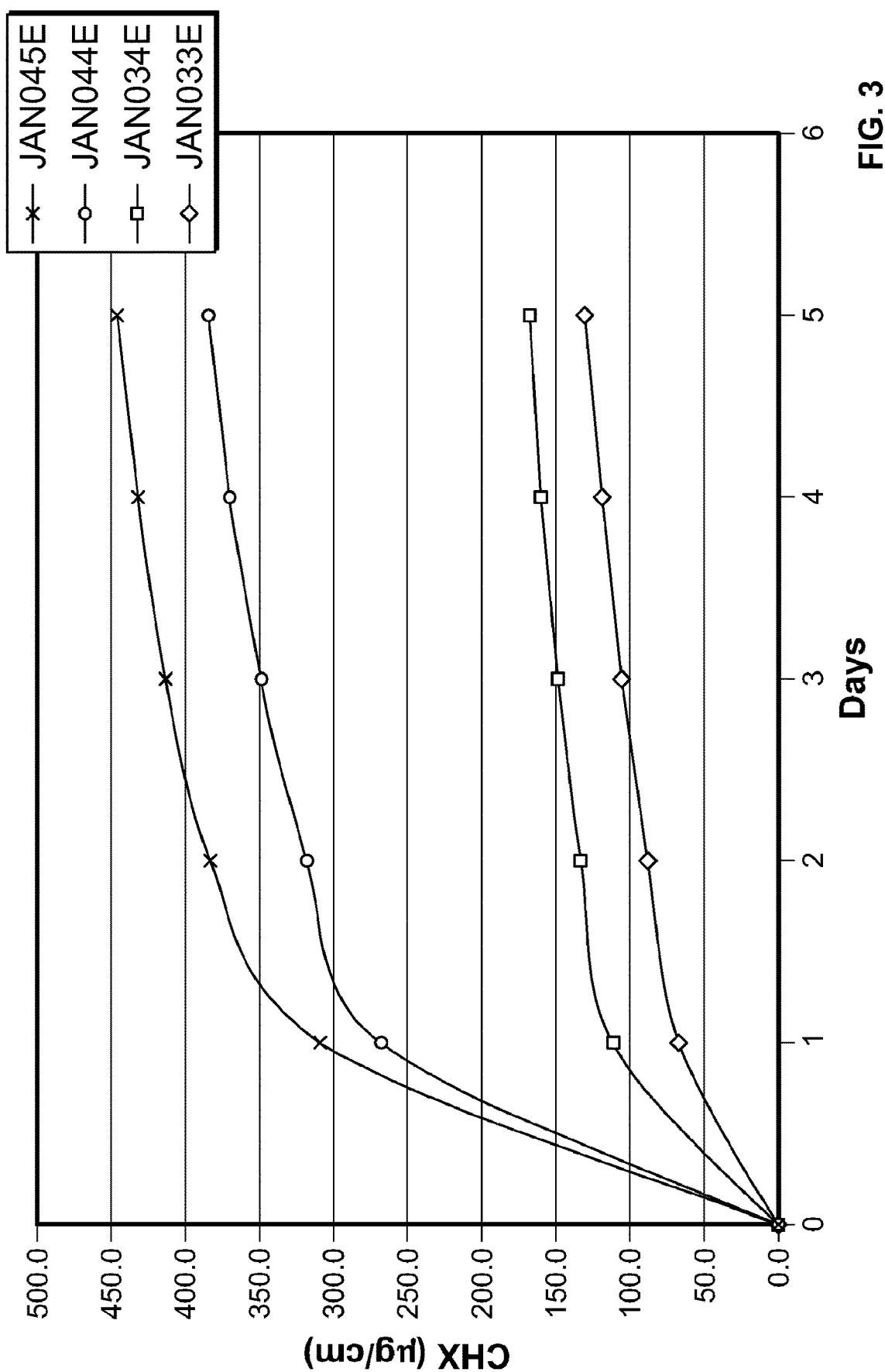

FIG. 3. Cumulative elution of chlorhexidine (micrograms/cm), where treatment of catheters was with 1.5% or 3.0% chlorhexidine.

Figure 4:
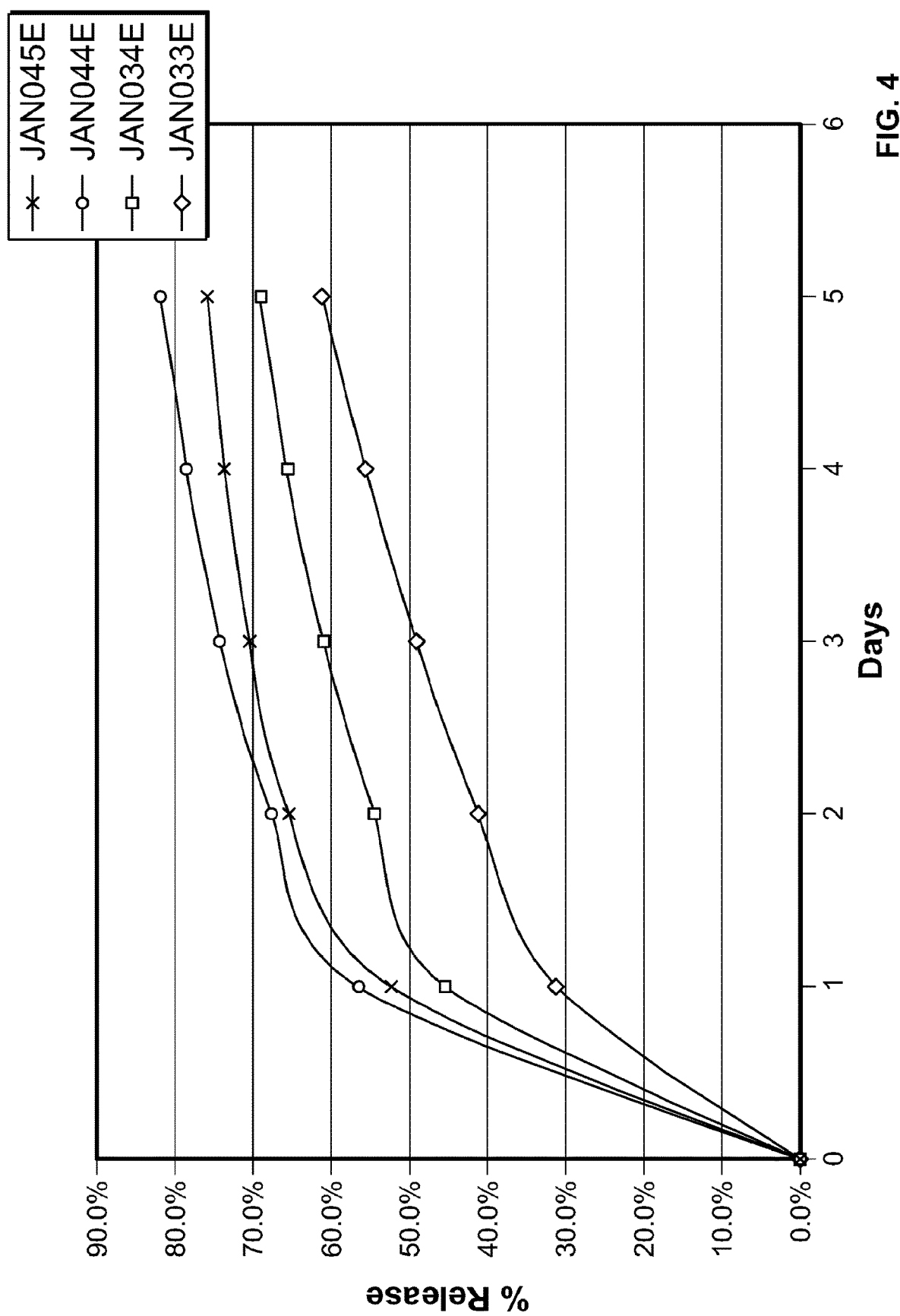

FIG. 4. Cumulative elution of chlorhexidine (percent release) over time, where treatment of catheters was with 1.5% or 3.0% chlorhexidine.

Figure 5:
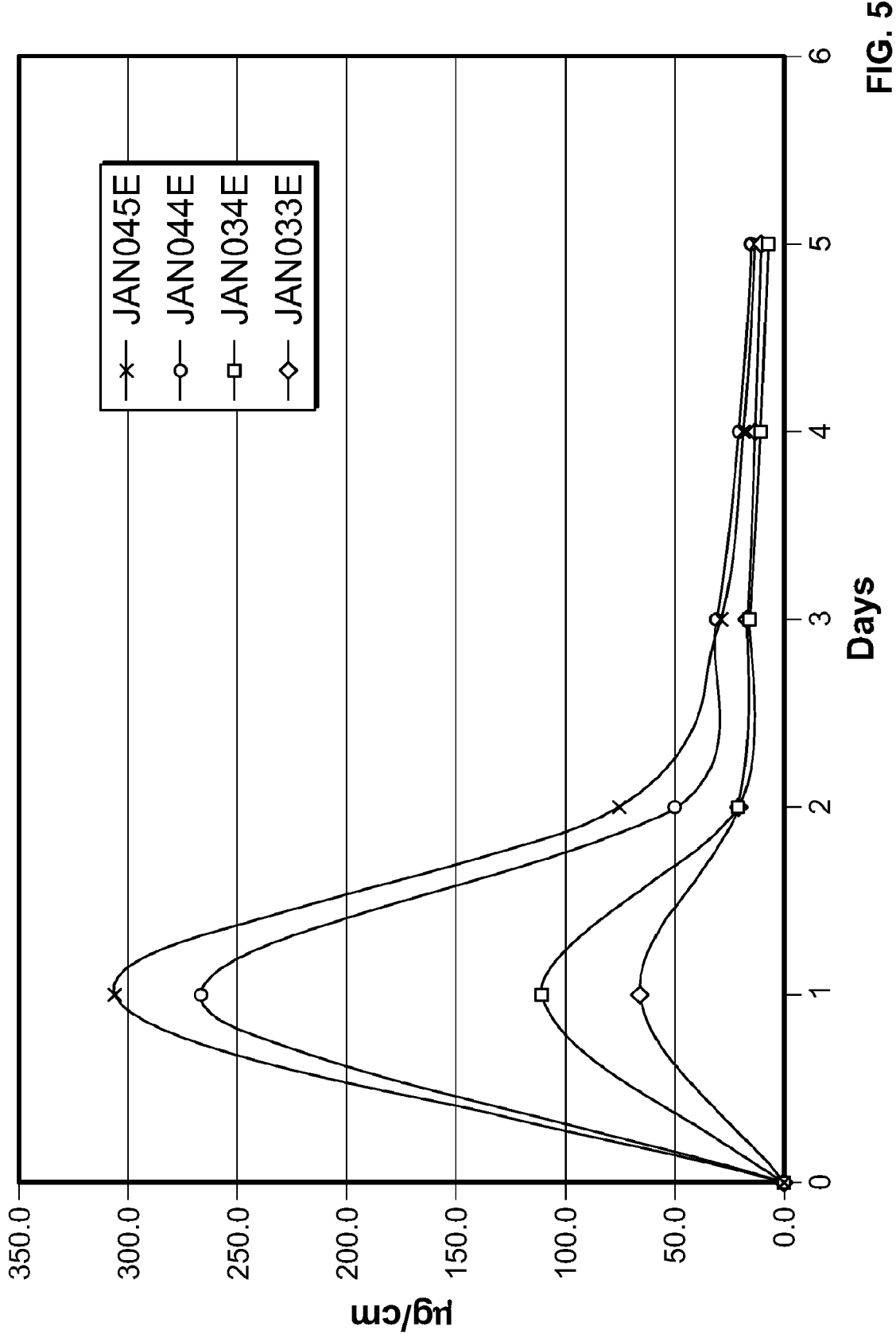

FIG. 5. Quantity of chlorhexidine eluted per day.

Figure 6:
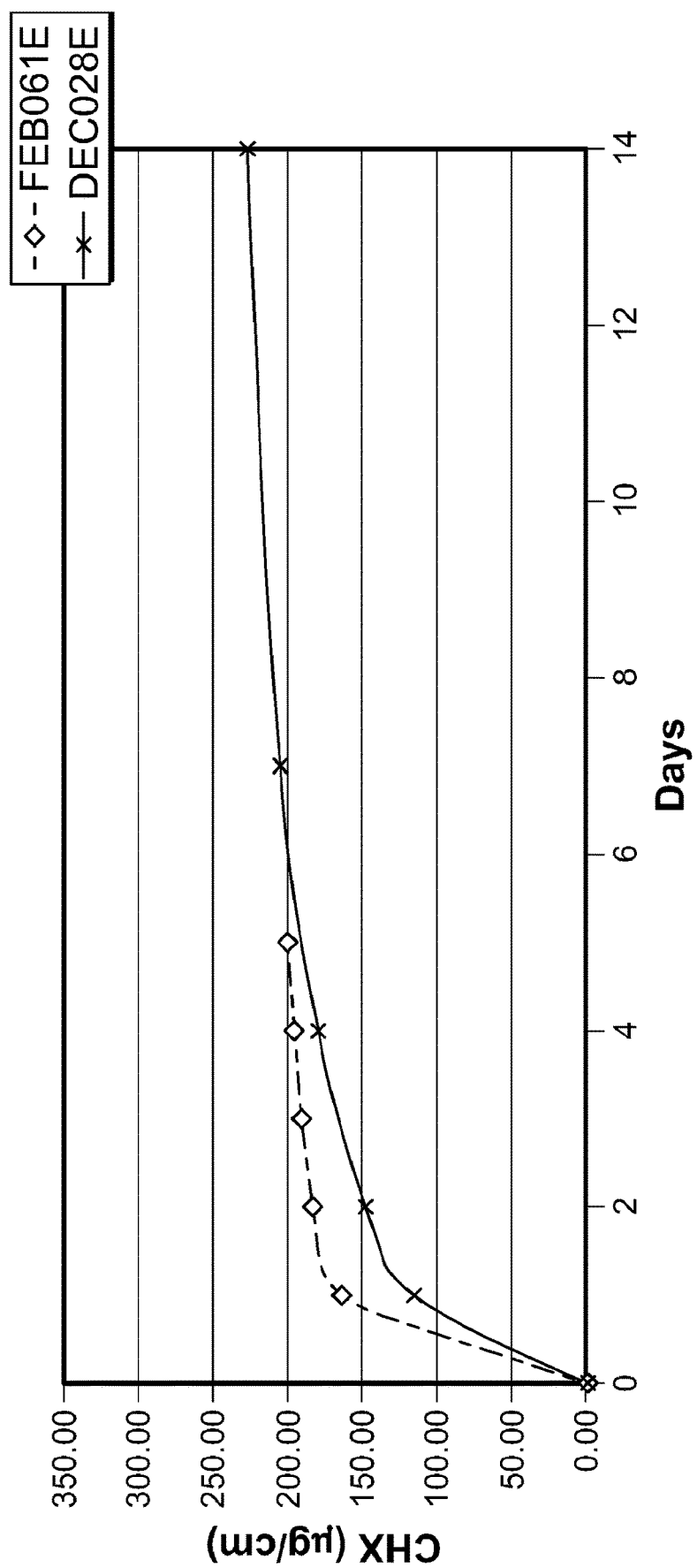

FIG. 6. Cumulative elution of chlorhexidine.

Figure 7:
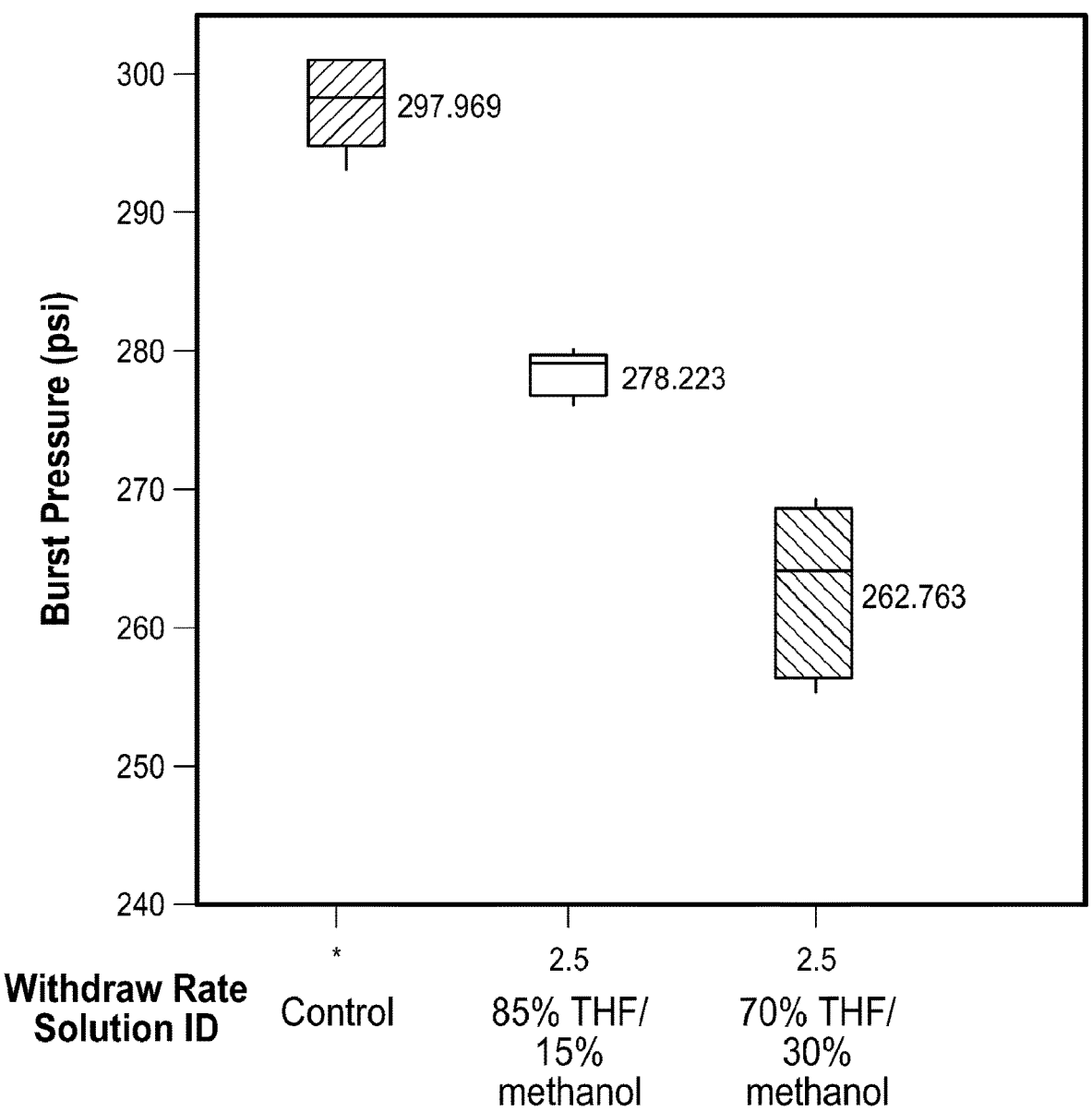

FIG. 7. Burst pressure (psi) of treated catheters.

Figure 8:
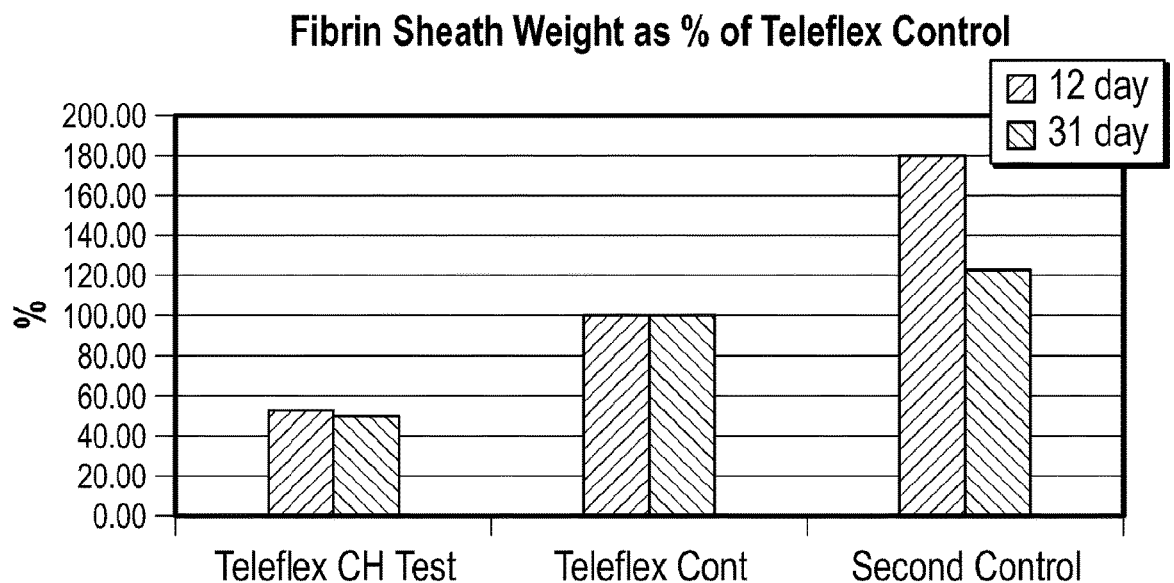

FIG. 8. Fibrin sheath weight as percent of control (non-infection model).

Figure 9:
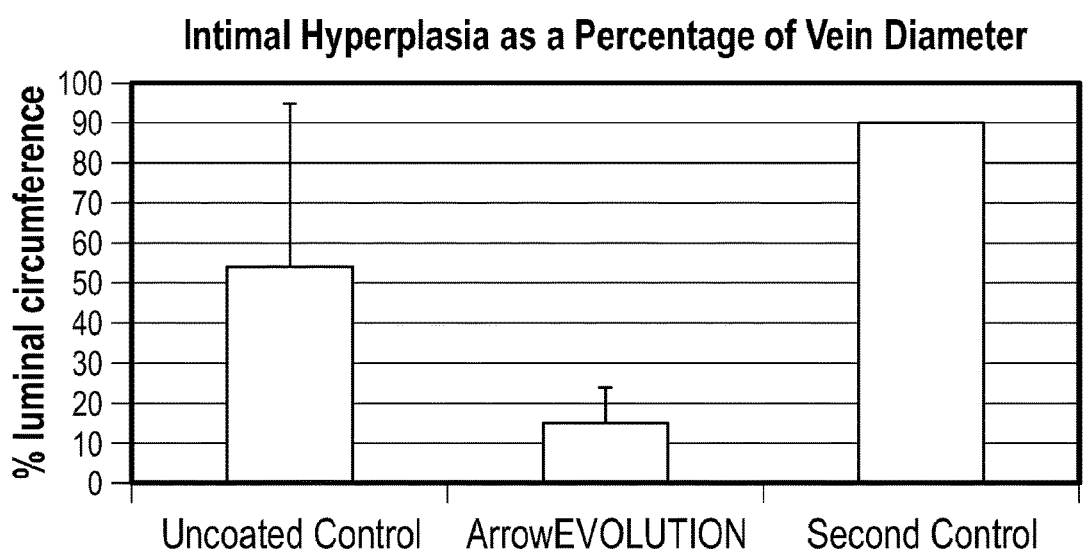

FIG. 9. Fibrin sheath weight as percent of control (infection model).

Figure 10:
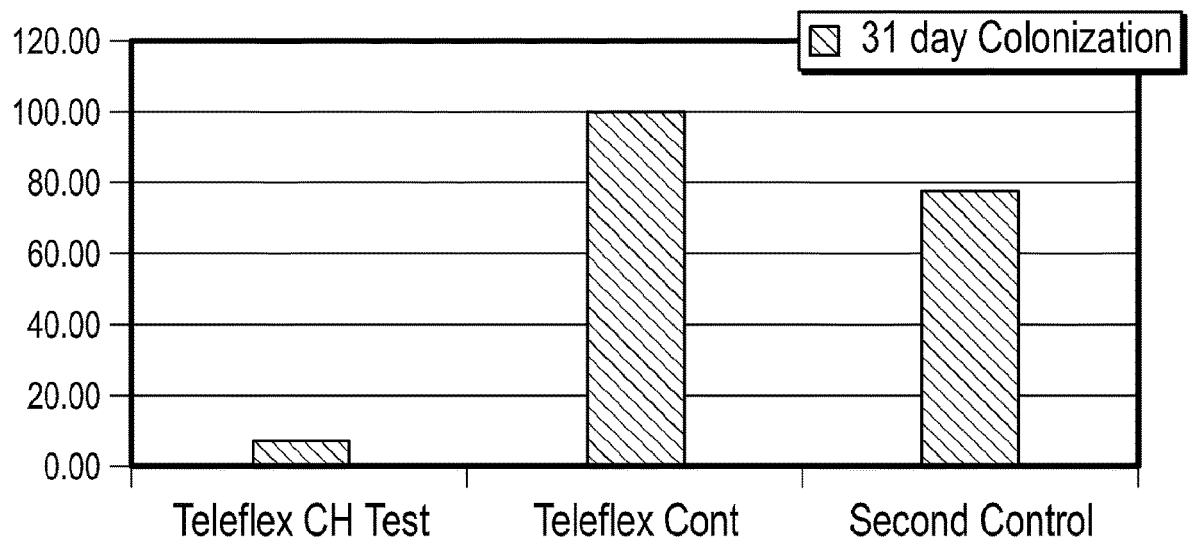

FIG. 10. Intimal hyperplasia as percentage of vein diameter.

DETAILED DESCRIPTION OF THE DISCLOSURE

The present disclosure provides formulations, as well as medical devices treated with or impregnated with, the formulations of the present disclosure. Catheters and other medical devices, treated or impregnated with an antimicrobial agent, and configured for use in different regions of the body, are provided. These include, for example, vascular catheters, epidural catheters, endotracheal tubes, and urinary catheters. Nanocomposites, membranes, films, sandwiches, tubes, and the like, are encompassed by the present disclosure (see, e.g., Fong, et al. (2010) Acta. Biomater. 6:2554-2556; Huynh, et al (2010) Eur. J. Pharm. Biopharm. 74:255-264; Berra, et al (2008) Intensive Care Med. 34:1020-1029).

In embodiments, the disclosure encompasses methods for bulk distribution, gradient distribution, and limited surface distribution. Methods for manufacturing medical devices where an agent such as chlorhexidine is bulk distributed, gradient distributed, or limited surface distributed, are available (see, e.g., U.S. Pat. No. 4,925,668 issued to Khan, et al, U.S. Pat. No. 5,165,952 issued to Solomon and Byron, and U.S. Pat. No. 5,707,366 issued to Solomon and Byron, all of which are incorporated herein by reference). In some aspects, the disclosed device excludes embodiments with bulk distribution.

The following terminology is for use in describing the concentration of any agent, for example, an anti-microbial agent, in a medical device, such as a catheter, or a related composition. The medical device has an external surface portion, and an internal volume portion, where a representational part of the internal volume comprises an area of the external surface portion. This representational part of the internal volume, in some embodiments, extends about 10 micrometers (um) down from the external surface into the interior, extends about 20 um, extends about 40 um, extends about 60 um, extends about 80 um, extends about 100 um, extends about 120 um, extends about 140 um, extends about 160 um, extends about 180 um, extends about 200 um, extends about 300 um, extends about 400 um, extends about 600 um, extends about 800 um, extends about 1000 um (1.0 mm), and the like. A selected representational part of the internal volume, for example, when sampled from the outer surface of a catheter or from an internal lumen of a catheter, contains the agent at a concentration of at least 5 micromolar (5 uM), at least 10 uM, at least 20 uM, at least 40 uM, at least 60 uM, at least 80 uM, at least 100 uM, at least 120 uM, at least 140 uM, at least 160 uM, at least 180 uM, at least 200 uM, at least 300 uM, at least 400 uM, at least 600 uM, at least 800 uM, at least 1000 uM (1.0 mM), at least 2 mM, at least 5 mM, at least 10 mM, at least 15 mM, at least 20 mM, at least 25 mM, at least 30 mM, at least 40 mM, at least 60 mM, at least 80 mM, at least 100 mM, at least 150 mM, at least 200 mM, at least 250 mM, and the like. In this context, the concentration unit of molarity is a surrogate for concentration of moles of agent per 100 cubic centimeters (one liter) of the selected internal volume of the medical device.

The disclosure encompasses a medical device treated with one or more of the presently described formulations, where the formulation contains a small molecule agent, such as chlorhexidine. For measurement, representative sample can be acquired by way of a sample that has a cubical conformation, a rectangular conformation, a cylindrical conformation, an amorphous conformation, as long as the sample is believed to be representative of the distribution (or concentration) of the agent in the region between the external surface and selected depth, or in a deeper region, for example, in a region between 50 micrometers deep and 200 micrometers deep.

Where chlorhexidine binds only to the surface of a medical device, such as a catheter, documentation of data on coating may be more meaningfully expressed in terms of micrograms chlorhexidine per square millimeter (and less meaningfully expressed in terms of micrograms chlorhexidine per cubic millimeter). The agent of the present disclosure is not limited to small molecules or to antimicrobials. What is encompassed is any agent of clinical use, or any agent that enhances one or more properties of the medical device, where the agent is substantially or completely soluble in the formulation. Thus, the agent can be a polymer with antimicrobial properties, where the polymer is substantially or completely soluble in the formulation.

The concentration can also be measured in situ, for example, with a technique involving fluorescence, radioactivity, or microbiological assays. Catheter is a non-limiting example. A microbiological assay configured for measuring the concentration of the amount of antimicrobial within a catheter can be measured as follows. A series of catheters, pre-impregnated with various concentrations of known antimicrobial, can be inoculated with the same quantity of a bacterium. The inoculated catheter can then be incubated under conditions suitable for growth of the bacteria, for example, including nutrients and a temperature of 37 degrees C. Following an incubation time of, for example, 1-7 days, the quantity of bacterial can then be measured. The amount of impregnated antimicrobial can be expressed in terms of a unit of percent maximal efficacy, or the amount of impregnated antimicrobial can be expressed with reference to a standard catheter containing a known quantity of antimicrobial. Methods are available for converting any organic molecule, such as chlorhexidine, into a corresponding radioactive molecule that contains tritium.

The present disclosure provides a formula that, when impregnated into a medical device, and when tested in the above microbiological assay, results in less than 80% maximal number of bacteria, less than 60%, less than 40%, less than 20%, less than 10%, less than 10%, less than 5%, less than 1%, less than 0.1%, less than 0.01%, less than 0.001%, less than 0.0001%, maximal number of bacteria. Maximal number of bacteria is measured with a control medical device, where the control medical device had been treated with solvents only (but not with any antimicrobial agent).

In some embodiments of the microbiological assay, the culturing medium is a complete nutrient medium that allows growth of the test organism. In other embodiments, the culturing medium is an incomplete nutrient medium that allows maintenance of the test organism, but does not support growth.

In embodiments that exclude, the present disclosure excludes a medical device or related composition, where the concentration is less than 5 micromolar (5 uM), less than 10 uM, less than 20 uM, less than 40 uM, less than 60 uM, less than 80 uM, less than 100 uM, less than 120 uM, less than 140 uM, less than 160 uM, less than 180 uM, less than 200 uM, less than 300 uM, less than 400 uM, less than 600 uM, less than 800 uM, less than 1000 uM (1.0 mM), less than 2 mM, less than 5 mM, less than 10 mM, less than 15 mM, less than 20 mM, less than 25 mM, less than 30 mM, less than 40 mM, less than 60 mM, less than 80 mM, less than 100 mM, and so on.

The hardness of the devices of the present disclosure, including hardness of specific features, such as a tip, wall, bump, tapered region, hub, wing, tab, conical region, bead-like region, can be measured by the durometer method and Shore hardness scale. See, e.g., U.S. Pat. No. 5,489,269 issued to Aldrich and Cowan, U.S. Pat. No. 7,655,021 issued to Brasington and Madden, and Eleni, et al. (2011) Effects of outdoor weathering on facial prosthetic elastomers. Odontology. 99:68-76, which are each individually incorporated herein by reference.

The present disclosure encompasses Shore A embodiments and Shore D embodiments. For example, a catheter, an internal lumen coating, an external coating, and such, can have (or can provide) a durometer value of about 40 to about 80 on a Shore A scale, about 45 to about 75 on a Shore A scale, about 50 to about 70 on a Shore A scale, about 55 to about 65 on a Shore A scale, or with a value of at least 10, at least 20, at least 30, at least 40, at least 50, at least 60, at least 70, at least 80, at least 90, at least 100, at least 120, at least 140, and the like, on a Shore A scale. Moreover, the dilator, a specific region or component of the dilator, or other device, such as a sheath, can have a value of less than 10, less than 20, less than 30, less than 40, less than 50, less than 60, less than 70, less than 80, less than 90, less than 100, less than 120, less than 140, and the like, on a Shore A scale. In other hardness embodiments, the disclosure provides a device (or a coating) with a durometer value of about 40 to about 80 on a Shore D scale, about 45 to about 75 on a Shore D scale, about 50 to about 70 on a Shore D scale, about 55 to about 65 on a Shore D scale, or with a value of at least 10, at least 20, at least 30, at least 40, at least 50, at least 60, at least 70, at least 80, at least 90, at least 100, at least 120, at least 140, and the like, on a Shore D scale. Moreover, the catheter, internal coating, or external coating, can have a value of less than 10, less than 20, less than 30, less than 40, less than 50, less than 60, less than 70, less than 80, less than 90, less than 100, less than 120, less than 140, and the like, on a Shore D scale.

At a given concentration of polymer in solution, where the polymer in solution is a component of a given formulation, the hardness value of the polymer can be chosen so that the solution of chosen polymer has a viscosity that is greater than that of a solution of a comparator polymer. In embodiments, the solution of chosen polymer has a viscosity that is at least 5% greater, at least 10%, at least 15%, at least 20%, at least 30%, at least 40%, at least 50%, at least 60%, at least 80%, at least 100% (twice as great), at least 1.5-fold, at least 2.0-fold, at least 4.0-fold, at least 6.0-fold, at least 8.0-fold, at least 10-fold, and the like, greater than that with comparator polymer.

At a given concentration of polymer in solution, where the polymer in solution is a component of a given formulation, the hardness value of the polymer can be chosen so that the solution of chosen polymer provides a mechanical adherence of the coating to the medical device body that is greater than that of a solution of a comparator polymer. Without implying any limitation, mechanical adherence of the coating can be measured by subjecting coated medical device to a number of flexing cycles, e.g., 1,000 cycles, 5,000, 10,000, 15,000, 50,000, 100,000, 150,000, 500,000 cycles, and the like. In embodiments, the solution of chosen polymer provides a mechanical adherence of coating to medical device body that is greater than that with comparator polymer, where mechanical adherence is at least 5% greater, 10%, 20%, 40%, 60%, 80%, 100% (twice that), 4-fold, 6-fold, 8-fold, 10-fold, at least 20-fold greater, and the like.

At a given concentration of polymer in solution, where the polymer in solution is a component of a given formulation, the hardness value of the polymer (or the concentration of the polymer in solution) can be chosen so that the solution of chosen polymer slows down release of chlorhexidine from the medical device. The slowing of release can be relative to a medical device coated with a comparator polymer (the comparator polymer can have a different hardness value). Alternatively, the slowing of release can be relative to a medical device, coated with the same polymer but at a lesser concentration. The viscosity of the solution that contains soluble polymer, can result in a coated medical device, where chlorhexidine release is less than 100% maximal rate of release, less than 95%, less than 90%, less than 80%, less than 70%, less than 50%, less than 20%, and the like.

The viscosity of solutions and formulations, including those comprising polyurethane can be measured using available instruments and methods. See, for example U.S. Pat. No. 8,017,686 issued to Buter, et al, and U.S. Pat. No. 5,091,205 issued to Fan, which are hereby incorporated by reference. The Brookfield viscometer is a standard instrument (Brookfield Engineering Laboratories, Middleboro, Mass.). Equipment and methods for burst tests are available. See, e.g., Uson Testra static burst tester; Uson, Houston, Tex. The burst test can be destructive or non-destructive.

Thermoplastic polyurethane (TPU) tubing, resins, and the like, are available for use in the present disclosure, for example, as a medical device such as a catheter, as a coating for the medical device, as a formula configured for use in coating the medical device, or as a medical device that is modified by coating with the formula. What is available is tubing, resins, and the like, having a hardness of 72A, 77A, 87A, 94A, 51D, 60D, 63D, 67D, 73A/78A, 83A/86A, 90A/95A, 93A/98A, 55D/65D, 63D/78D, 73D, 75D/82D (Tecoflex® series); and 75A, 85A, 94A, 54D, 64D, 69D, 74D, 75D, 77A/83A, 87A/88A, 97A/97A, 55D/64D, 67D/75D, 70D, 75D, 77D/84D (Tecothane® series) (Lubrizol's Engineered Polymers for Medical and Health Care; Lubrizol Corp, Cleveland Ohio). Guidance on medical polymers, including polyurethane, is available, for example, from Polymer Membranes/Biomembranes (Advances in Polymer Science), ed. by Meier and Knoll, Springer, 2009; Lubricating Polymer Surfaces by Uyama, CRC Press, 1998; and Polymer Grafting and Crosslinking, ed. by Bhattacharya, et al, Wiley, 2008.

Reagents, including high purity solvents, as well as polymer resins such as 95A resin, can be acquired from Lubrizol Corp., Cleveland, Ohio; Microspec Corp., Peterborough, N.H.; Polaris Polymers, Avon Lake, Ohio; U.S. Plastic Corp., Lima, Ohio; Sigma-Aldrich, St. Louis, Mo.; E.I. du Pont de Nemours and Company, Wilmington, Del.; Dow Chemical Co., Midland, Mich. Polyurethane of durometer 95A is disclosed, for example, by US 2010/0082097 of Rosenblatt, et al, U.S. Pat. No. 6,517,548 issued to Lorentzen Cornelius, et al, and by U.S. Pat. No. 2011/0054581 of Desai and Reddy. Each of these patents and published patent applications is hereby incorporated herein by reference.

An anti-microbially effective quantity of an anti-microbial agent can be measured by a number of non-limiting methods. The agent can be solubilized in water or other aqueous solution, solubilized in a solvent such as dimethylsulfoxide (DMSO) and then dispersed into an aqueous solution, dispersed in an aqueous solution with sonication, or dispersed into an aqueous solution by associating with albumin. Where the anti-microbial agent resides in the surface of, or has been impregnated into, or has been bulk incorporated into, a medical device, the agent can be extracted from the device using a solvent (e.g., water, methanol, tetrahydrofuran, DMSO, and the like), or crushed or pulverized, and then extracted with solvent. Then, the solubilized or extracted anti-microbial can be tested for anti-microbially effective activity using chemical methods, e.g., high pressure liquid chromatography (HPLC) or microbiological assays, e.g., in solution or agar-based, using methods well known by the skilled artisan. Alternatively, anti-microbial efficacy of the medical device can be assessed by inoculating the medical device with a microbe, and by monitoring the ability of the anti-microbial agent to reduce growth, to reduce attachment, or to kill, the microbe. Anti-microbial activities taking place on the surface of the medical device, or within the matrix or pores of the medical device, can be assessed by light microscopy or electron microscopy, using methods well known to the skilled artisan. A medical device containing an anti-microbially effective amount of an anti-microbial agent can be measured by detecting the number of microorganisms that colonize the surface of a medical device or that colonize pores or a matrix of a medical device. Alternatively, and without limitation, anti-microbially effective can be measured by incubating the medical device in a liquid medium, or an agar medium, and by detecting the number of microorganisms that colonize the surface of medical device, or that colonize a pre-determined area or volume apart from the surface of the medical device, for example, an area that is 0 mm to 1 mm away from the surface of the medical device, that is 1 mm to 3 mm away, from 0 mm to 3 mm away, 2 mm to 5 mm away, from 0 mm to 5 mm away, from 2 mm to 20 mm away, and the like. Control medical devices can be treated with sham formulation only (no anti-microbial) or can be treated with an active control.

Methods and equipment are available to the skilled artisan for measuring structures, properties, and functions, of medical devices, such as catheters. The following references disclose methods and equipment for measuring, for example, tensile strength, force at break, elastic behavior, plastic behavior, microscopy for detecting microbial colonies or biofilms residing on the surface of catheters, microbiological assays for measuring influence of antimicrobials. See, e.g., Aslam and Darouiche (2010) Infect. Control Hosp. Epidemiol. 31:1124-1129; Hachem et al (2009) Antimicrobial Agents Chemotherapy 53:5145-5149; Venkatesh et al (2009) J. Medical Microbiol. 58:936-944, which are hereby incorporated herein by reference. Methods and equipment for measuring tensile strength, elongation at break, and other properties of medical devices, are available. See, e.g., U.S. Pat. No. 6,039,755 issued to Edwin et al, and U.S. Pat. No. 7,803,395 issued to Datta et al, which are incorporated herein by reference. Above a limiting stress, called the elastic limit, some of the strain is permanent. In going beyond the elastic limit, a solid can either fracture suddenly or deform in a permanent way (see, e.g., Ashby M F, Jones D R H (2012) Engineering Materials 1, 4.sup.th ed., Elsevier, New York, pp. 115-133).

EXAMPLES

Internal Formulation

Formulations and methods for preparing the internal solution are disclosed, as follows. Formulation of internal solution is shown (Table 1).

TABLE-US-00001 TABLE 1 Internal solution. Methyl-ethyl-ketone about 2000 grams Methanol about 400-500 grams Acetone about 600-700 grams Chlorhexidine diacetate about 50 grams Chlorhexidine free base about 50 grams The reagents are chlorhexidine base, chlorhexidine diacetate, methyl-ethyl-ketone (MEK), methanol (ACS grade), and acetone. As a general statement, without intending any limitation, methanol can prevent precipitation of chlorhexidine to a greater extent than certain other solvents.

Elution Studies of Internally Coating of Internally Coated Catheter

For studies of elution of material from the internal coating of the dipped catheter, elution of material such as chlorhexidine was measured by soaking the catheter in citrated plasma.

Formulation pH, Precipitation of Chlorhexidine, and Chlorhexidine Content

Readings of pH, for various formulations, were conducted shortly after a test strip was wetted with a coating solution. A "dry" reading was recorded after the test strip had completed a drying cycle. Wet and "dry" readings for various formulations were as follows. The trivial names of the formulations are MAR091, MAR092, MAR093, and MAR094. The pH readings were MAR091 (wet pH 7, dry pH 10), MAR092 (wet pH 7, dry pH 8), MAR093 (wet pH 6, dry pH 6), and MAR094 (wet pH 6, dry pH 6). Related work demonstrated that solutions with alkaline pH values let to precipitation of chlorhexidine. The formulations included the following amounts (%) of MEK, methanol, acetone, CHA, and CHX, respectively. MAR091 (65%; 30%; 0%; 50%; 50%). MAR091 also included 5% acetonitrile. MAR092 (65%; 30%; 0%; 50%; 50%). MAR092 also included 5% THF. MAR093 (65%; 15%; 20%; 50%; 50%). MAR094 (65%; 20%; 15%; 50%; 50%). Chlorhexidine content, in terms of micrograms/cm, of treated catheters was measured. Treated catheters had the indicated chlorhexidine content: MAR091 (23 micrograms/cm), MAR092 (26 micrograms/cm), MAR093 (30 micrograms/cm), and MAR094 (29 micrograms/cm).

The disclosure provides one or more formulations, where the pH is less than 9.0, less than 8.5, less than 8.0, less than 7.5, less than 7.0, less than 6.5, or where the pH is between 5.0-9.0, between 5.0-8.5, between 5.0-8.0, between 5.0-7.5, between 5.0-7.0, between 5.0-6.5, between 5.0-6.0, and the like. Formulation can be applied to a commercially available, e.g., pH indicator paper, pH test strips, or pH indicator strips from Sigma Aldrich, St. Louis, Mo. Moisture present in the formulation and/or in the pH paper is sufficient to obtain a pH reading of formation. The skilled artisan can acquire pH value of a formulation that is dried on a substrate, or a pH value of a formulation that is non-aqueous, by adding distilled water, e.g., 0.05 mL, 0.10 mL, 0.20 mL, 0.5 mL, 1.0 mL, of neutral, buffer-free distilled water, and by dissolving the formulation in the distilled water.

External Formulation

Formulation and method for preparing external solution is disclosed, as follows. Formulation is disclosed (Table 2).

TABLE-US-00002 TABLE 2 External formulation Tetrahydrofuran (THF) about 2000-2500 grams Methanol about 200-300 grams Polyurethane 95A about 100-200 grams Chlorhexidine diacetate about 50 grams Elution Studies of External Coating of Externally Coated Catheter For studies of elution of material from the external coating of the dipped catheter, elution of material such as chlorhexidine was measured by soaking the catheter in normal saline.

Assay Method for Chlorhexidine

Chlorhexidine was extracted form samples of catheters, or of other medical devices. Analysis used high pressure liquid chromatography (HPLC) using a column (Agilent, Santa Clara, Calif.). Detection of chlorhexidine was with light at 280 nm. The method was standardized using known standards of chlorhexidine (75.0 micrograms/mL).

Measuring Chlorhexidine Content of Treated Catheters

Table 3 discloses the chlorhexidine content (micrograms/cm) where total chlorhexidine in the treating solution was 0.5 wt. % or 1.5 wt. %, as indicated, and where chlorhexidine takes the form of 100% chlorhexidine diacetate (CHA), or where the chlorhexidine takes the form of 50/50 chlorhexidine diacetate (CHA)/chlorhexine base (CHX), as indicated. The following concerns the content of chlorhexidine in the treated catheters, prior to conducting time-course elution experiments. As shown in Table 3, as the CHA was increased (in the ratio of CHA to CHX in the treatment solution) the content on the catheter slightly decreased. The slight drop in content observed when comparing the 50/50 CHA/CHX solutions and 100% CHA solutions is attributed to the fact that a portion of the weight of CHA (about 20%) is acetate, whereas the weight of CHX is pure chlorhexidine. Table 3 discloses the concentrations at t=zero days, as it applies to the 3-day time course experiments shown in FIG. 1 and FIG. 2.

TABLE-US-00003 TABLE 3 Chlorhexidine content of treated catheters. Trivial Chlorhexidine name of Solution for treating catheter each content solution with polyurethane resin (micrograms/cm) JAN031 0.5 wt % 50/50 85% THF, 58.20 CHA/CHX 15% methanol JAN030 0.5 wt % 100% CHA 85% THF, 51.17 15% methanol JAN032 0.5 wt % 10/90 85% THF, 61.98 CHA/CHX 15% methanol JAN034 1.5 wt % 50/50 85% THF, 164.85 CHA/CHX 15% methanol JAN033 1.5 wt % 100% CHA 85% THF, 151.42 15% methanol JAN035 1.5 wt % 10/90 85% THF, 169.06 CHA/CHX 15% methanol FIG. 1 reveals cumulative elution of chlorhexidine (micrograms/cm) over time, where treatment of catheters was with solutions of 0.5% or 1.5% chlorhexidine. Elution was followed for three days. The percentage refers to the total amount, by weight, of the chlorhexidine in the treatment solution. The solutions of chlorhexidine were 100% chlorhexidine diacetate (CHA), 50/50 chlorhexidine diacetate/chlorhexidine base (CHA/CHX), or 10/90 CHA/CHX. Lower rates of release were found with 0.5% wt % (diamonds, squares, triangles), as compared to data where catheters were treated with solutions of 1.5% (X (upper X curve), X (lower X curve), X (lower filled circles curve). The lowest rate of elution was where the coating procedure used 100% CHA, while the fastest rate of elution occurred where the coating procedure used 10/90 CHA/CHX. Thus, where the goal is to acquire a medical device with prolonged time-release, treatment solutions with 100% CHA is preferred.

FIG. 2 illustrates cumulative elution of chlorhexidine (percent release) over time, where treatment of catheters was with 0.5% or 1.5% chlorhexidine. Elution was monitored for three days. The lowest rate of elution was where the coating procedure used 100% CHA, while the fastest rate of elution occurred where the coating procedure used 10/90 CHA/CHX.

FIG. 3 demonstrates cumulative elution of chlorhexidine (micrograms/cm), where treatment of catheters was with 1.5% or 3.0% chlorhexidine. Elution was followed for five days. Table 4 lists the treatment solutions, and the initial chlorhexidine content of the catheters with the four treatments. This represents a different set of treated catheters than the set represented by Table 3. Table 4 shows the concentration at t=zero days, in the 5-day time course experiments shown in FIG. 3, FIG. 4, and FIG. 5. Where the treatment solution contained 100% CHA, the rate of elution was slower, as compared to elution where the treatment solution contained 50/50 CHA/CHX (FIG. 3). The slower elution with the 100% CHA catheters was found where treatment was with the lower total concentration. Where the higher total concentration (3.0%) of chlorhexidine was used in the treatment solution, treatments with 100% CHA resulted in lower rates of elution, during the time-course test (FIG. 3).

To summarize, slower rates of elution were found with 3 percent of 100% CHA (X-points), as compared with 3 percent of 50/50 CHA/CHX (open square-points). Also, slower rates of elution were found with 1.5 percent 100% CHA (closed diamond-points), when compared with 1.5 percent 50/50 CHA/CHX (closed square-points). Thus, where the goal is to acquire a medical device with prolonged time-release, treatment solutions with 100% CHA is preferred.

Photographs of catheters treated with formulations JAN045, JAN034, JAN044, AND JAN033 were taken. The photographs disclose shark skin appearance, whiteness caused by flexing, tiny bubbles, small surface defects, and absence of defects.

In embodiments, what is provided is a medical device, e.g., catheter, cannula, or introducer, with chlorhexidine content of at least 150 micrograms/cm, at least 175, at least 200, at least 225, at least 250, at least 275, at least 300, at least 325, at least 350, at least 375, at least 400, at least 425, at least 450, at least 475, at least 500, at least 525, at least 550, at least 575, at least 600, at least 625, at least 650, at least 675, at least 700, and the like, micrograms/cm. In exclusionary embodiments, the invention excludes a medical device where the chlorhexidine content (micrograms/cm) is less than 650, 625, 600, 575, 550, 525, 500, 475, 450, 425, 400, 375, 350, 325, 300, 275, 250, 225, 200, 175, 150, 125, 100, 75, 50, and the like, micrograms/cm.

TABLE-US-00004 TABLE 4 Chlorhexidine content of treated catheters. Trivial Chlorhexidine name of Solution for treating catheter. All content solution solutions contained polyurethane resin. (micrograms/cm) JAN033 1.5 wt % 100% CHA 85% THF, 200.5 15% methanol JAN034 1.5 wt % 50/50 85% THF, 227.4 CHA/CHX 15% methanol JAN044 3.0 wt % 100% CHA 85% THF, 430.5 15% methanol JAN045 3.0 wt % 50/50 85% THF, 488.1 CHA/CHX 15% methanol FIG. 4. Cumulative elution of chlorhexidine (percent release) over time, where treatment of catheters was with 1.5% or 3.0% chlorhexidine. Elution was followed for five days. Table 2 discloses the treatment solutions and initial chlorhexidine content of the catheters, with each of the four treatments. Where the treatment solution contained 100% CHA, the rate of elution was slower, as compared to elution where the treatment solution contained 50/50 CHA/CHX (FIG. 4). The slower elution with the 100% CHA catheters was found where treatment was with the lower total concentration. But with where the treatment solution had the higher total concentration of chlorhexidine, the 100% CHA catheters showed a somewhat higher elution rate, as compared with the 50/50 CHA/CHX catheters. (FIG. 4).

FIG. 5 demonstrates the quantity of chlorhexidine eluted per day. In other words, the data presented represent results on a per day basis (not cumulative results). Table 4 lists the treatment solutions and initial chlorhexidine content of the catheters, with each of the four treatments. In all tests, where the treatment solution contained 100% CHA, elution occurred at a slower rate than where treatment solution contained 50/50 CHA/CHX.

Surface Characteristics of Treated Catheters

Catheters coated according to Table 4 were evaluated. Table 4 discloses four types of treatment solutions. With 3.0% chlorhexidine 50/50 CHA/CHX, the surface was rough and resembled that of shark skin. When the catheter was flexed, the area that was flexed turned white from stress whitening. The other catheters had a better appearance, though the 3.0 wt % chlorhexidine 100% CHA had small bubbles on the surface, and 1.5% chlorhexidine 100% CHA had small defects on the surface.

Effect of Different Percentages of Tetrahydrofuran and Methanol in the Treatment Solutions Changing the percentages of tetrahydrofuran (THF) and methanol, in treatment solutions, resulted in changes in various characteristics of the catheters, as measured after treatment. Treatment solutions containing 70% THF/30% methanol or 85% THF/15% methanol were tested. Table 5 identifies these non-limiting solutions.

TABLE-US-00005 TABLE 5 Solutions for treating catheters. Each solution had polyurethane resin. Total wt Trivial % of name of chlor-Ratio of Quantities of THF, methanol, solution hexidine CHA/CHX and resin FEB061 2.0 wt % 50/50 70% THF, 30% methanol CHA/CHX DEC028 2.0 wt % 50/50 85% THF, 15% methanol CHA/CHX The treated catheters were subjected to time-course tests for elution of chlorhexidine. FIG. 6 demonstrates that samples prepared with the lower THF solution had a higher initial release of chlorhexidine, while samples prepared with higher THF solution had lower initial release rate (FIG. 6). Thus, where the goal is to acquire a medical device with prolonged time-release, treatment solutions with a lower relative THF concentration is preferred.

FIG. 7 discloses results from burst pressure (psi) experiments of uncoated and coated catheters. Catheters were subject to no treatment (control), to treatment with higher THF solution, or to treatment with lower THF solution. The higher THF solution contained 85% THF, 15% methanol, overall chlorhexidine 2 wt. %, 50/50 CHA/CHX, and polyurethane resin. The lower THF solution contained 70% THF, 30% methanol, overall chlorhexidine 2 wt. %, 50/50 CHA/CHX, and polyurethane resin.

FIG. 7 shows the burst pressure of uncoated and coated catheters. Burst pressure was lower with the 70% THF/30% methanol solution, and higher with the 85% THF/15% methanol solution. The drop in burst strength with lower THF content may have been due to the increase in methanol content, where the increased methanol provoked deterioration of the catheter. The results demonstrate that high THF or lower methanol are preferred for a more robust burst strength.

Fibrin Weight and Intimal Hyperplasia

The following discloses results with peripherally inserted central catheters (PICC) using a preferred formulation, and two control formulations for coating and/or impregnating. Without implying any limitation, an infection model can involve rabbits with a bacterial challenge to a catheter by inoculating the insertion site with about 1 mL of inoculum of *Staphylococcus aureus*. Catheters can be anchored to the skin with adhesive tape and sutures. Infiltration of lumen of blood vessel with neutrophils, macrophages, or other indicia of inflammation can be measured. Location of bacterial accumulation in wall of blood vessel can be detected and quantified. In one embodiment, the indwelling catheter can be maintained in rabbit for two weeks, three weeks, four weeks, and so on. In the weight measurements, the reported weight was a mixture of visible clot/thrombus and fibrin sheath. The weight was measured after removal from the catheter. Any thrombus formation was removed from the catheter surface and weight in gram units.

Infection Models

Regarding the infection model, two sheep studies were run and inserted with coated products and uncoated products (separate groups) in their jugular veins with tip placement in superior vena cava. At 31 day, they were sacrificed to harvest vessels and catheters to evaluate amount of thrombus on catheter external surfaces. Infection model included introduction of *S. aureus* at insertion site to initiate infection to evaluate the impact of thrombus accumulation on catheter surfaces in presence of infection. The non-infection model did not include this step.

FIG. 8 discloses fibrin sheath weight as percent of control, using a non-infection model. Compared to the two control catheters, catheters coated with preferred formulation showed the least increase of fibrin sheath weight, in the non-infection model.

FIG. 9 discloses fibrin sheath weight as percent of control, using an infection model. Compared to the two control catheters, catheters coated with preferred formulation showed the least increase of fibrin sheath weight, in the infection model.

FIG. 10 discloses results from a study of intimal hyperplasia as percentage of vein diameter. Compared to the two control catheters (coated control; uncoated control), catheters coated with preferred formulation showed the lowest value for intimal hyperplasia. The time from was 31 days of catheter indwelling, followed by harvesting of vessels. Intima thickness was measured on histology slides.

In embodiments, preferred formulations result in a reduction by at least 10%, by at least 15%, by at least 20%, by at least 30%, by at least 40%, by at least 50%, by at least 60%, by at least 70%, by at least 80%, by at least 90%, when compared to non-treated catheter, of one or more of fibrin content, increase in intimal thickness, inflammation (e.g., white blood cell count in intima), or thrombogenicity. In embodiments, preferred formulations result in a reduction by at least 10%, by at least 15%, by at least 20%, by at least 30%, by at least 40%, by at least 50%, by at least 60%, by at least 70%, by at least 80%, by at least 90%, when compared to catheter treated, coated, or impregnated, with alternate formulation, of one or more of fibrin content, increase in intimal thickness, inflammation (e.g., white blood cell count in intimal), or thrombogenicity.

While the method and apparatus have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference.

Finally, all references listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant.

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

What is claimed is:

1. A method of coating a medical device, the method comprising the steps of:
   coating an interior of the medical device with a first solution consisting of:
      methyl-ethyl-ketone (50-70%); methanol (10-20%); acetone (15-25%);
      chlorhexidine diacetate (1%); and chlorhexidine free base (1%); and
   coating an exterior of the medical device with a second solution consisting of:
      tetrahydrofuran (THF) (70-90% by weight); methanol (5-15%); polyurethane (1-15%); chlorhexidine diacetate (1%); and chlorhexidine free base (1%), wherein the medical device does not comprise triclosan, silver salt, or zinc and the medical device does not further comprise an anti-thrombogenic agent and, wherein in use and with continued residence in a subject for at least one week, thrombogenesis occurs at a reduced rate of thrombus formation, wherein the reduced rate is tested by comparing the rate (X thrombi/week) of thrombus formation associated with said medical device, with the rate (Y thrombi/week) of thrombus formation associated with a corresponding medical device that does is not coated or impregnated with chlorhexidine, wherein X is less than 70% of Y.

2. The method according to claim 1, wherein X is selected from one of less than 90% of Y, and less than 80% of Y.

3. The method according to claim 1, wherein the medical device comprises one or more of a catheter, cannula, introducer, dilator, or sheath.

4. The method according to claim 3, wherein the medical device has a burst pressure that is selected from at least 250, at least 260, at least 270, at least 280, at least 290, and at least 300 pounds per square inch (psi).

5. The method according to claim 3, wherein the medical device has an internal volume portion having a concentration of chlorohexidine that ranges from at least 5 uM.

* * * * *